(12) United States Patent
Lee et al.

(10) Patent No.: US 7,649,124 B2
(45) Date of Patent: Jan. 19, 2010

(54) SIMULATED MOVING BED ADSORPTIVE SEPARATION PROCESS USING A PLURALITY OF ADSORPTION CHAMBERS IN PARALLEL AND CRYSTALLIZER AND DEVICE USED THEREIN

(75) Inventors: Jin-Suk Lee, Chungcheongnam (KR); Nam-Cheol Shin, Chungcheongnam (KR)

(73) Assignee: Samsung Total Petrochemicals Co, Ltd., Seosan-Shi, Chungcheongnam Province (KR)

( * ) Notice: Subject to any disclaimer, the term of this patent is extended or adjusted under 35 U.S.C. 154(b) by 596 days.

(21) Appl. No.: 11/613,553

(22) Filed: Dec. 20, 2006

(65) Prior Publication Data

US 2008/0149565 A1 Jun. 26, 2008

(30) Foreign Application Priority Data

Dec. 26, 2005 (KR) .................. 10-2005-0129459

(51) Int. Cl.
*C07C 7/135* (2006.01)

(52) U.S. Cl. ................ 585/828; 585/822; 585/826; 585/812; 422/139; 422/141; 422/154; 422/155

(58) Field of Classification Search ............. None
See application file for complete search history.

(56) References Cited

U.S. PATENT DOCUMENTS

| 4,326,092 A | | 4/1982 | Neuzil |
|---|---|---|---|
| 4,434,051 A | * | 2/1984 | Golem .................. 210/264 |
| 4,705,627 A | * | 11/1987 | Miwa et al. .............. 210/264 |
| 5,382,747 A | | 1/1995 | Kulprathipanja |
| 5,470,464 A | * | 11/1995 | Priegnitz ............... 210/198.2 |
| 5,470,482 A | * | 11/1995 | Holt ..................... 210/662 |
| 5,705,061 A | * | 1/1998 | Moran ................. 210/198.2 |
| 6,407,303 B1 | * | 6/2002 | O'Brien et al. ........... 585/738 |
| 7,514,590 B1 | * | 4/2009 | Rice ...................... 585/738 |
| 2006/0273013 A1 | * | 12/2006 | Chin et al. ............. 210/656 |

FOREIGN PATENT DOCUMENTS

KR 20010051842 6/2001

* cited by examiner

*Primary Examiner*—Tam M Nguyen
(74) *Attorney, Agent, or Firm*—Barlow, Josephs & Holmes, Ltd.

(57) ABSTRACT

Provided is a process for adsorptive separation of p-xylene from an aromatic hydrocarbon mixture comprising other isomers of xylene, and a device used therein. More specifically, the present invention provides a separation process employing simulated moving bed (SMB) adsorptive chromatography, characterized by subjecting the extracts eluted from a plurality of adsorption chambers arranged in parallel, to a crystallizer for additional separation, thereby improving productivity, and a device used therein.

6 Claims, 3 Drawing Sheets

SIMULATED MOVING BED ADSORPTIVE SEPARATION PROCESS USING A PLURALITY OF ADSORPTION CHAMBERS IN PARALLEL AND CRYSTALLIZER AND DEVICE USED THEREIN

FIELD OF THE INVENTION

The present invention relates to a separation process for adsorptive separation of p-xylene from an aromatic hydrocarbon mixture comprising other types of xylene isomers, and a device used therein, more specifically to a separation process employing simulated moving bed(SMB) adsorptive chromatography, characterized by subjecting the extracts eluted from a plurality of adsorption chambers arranged in parallel, to a crystallizer for additional separation, thereby improving productivity, and a device used therein.

BACKGROUND OF THE INVENTION

Conventional batch chromatography is a separation process which uses a principle of adsorption mechanism. Since it is suitably used for separation with high purity, assays carried out in a laboratory and the like, it is widely used in a separation or purification process of biosynthetic compounds with high purity, fine chemical compounds, food additives and the like. However, such separation processes using batch chromatography have some problems such that it requires a large amount of solvent used as a mobile phase; separation of a component is hardly achieved when the component to be separated has a similar adsorption property; and it is not appropriately used for separation in massive amount and continuous separation.

In order to solve these problems, a true moving bed (TMB) adsorptive separation process has been suggested in literatures such as Korean laid-open patent application No. 2001-51842 and the like. The TMB process introduces the concept of a counter current flow which has been efficiently used in various processes such as heat exchange and extraction, in which a flow which is counter to the flow direction of the mobile phase is applied to the stationery phase, thus when a mixed solution intended to be separated is fed into a column, a component which has stronger adsorption tendency to the stationery phase comes out of the column along with the flow of the stationery phase, and another component which has lower adsorption tendency to the stationery phase comes out of the column along the flow of the mobile phase. Therefore, this process is advantageous in that it is possible to obtain pure substance as long as two components can be separated at each end point of the concentration distribution curves of the two components, although they have not so much different separability In the meantime, it also has disadvantages such that the amount of a filling material should be increased as compared to the conventional fixed type separation process, and work in normal state is hardly achieved owing to the friction and leakage of the filling material.

For overcoming these problems of the TMB process, a simulated moving bed (SMB) adsorptive separation process has been developed. The SMB process solves the problems related to the flow of a stationery phase in the TMB process, with the simulation of the counterflow of the solid phase by filling and fixing the adsorbent that is a stationery phase into a column and stepwise moving the ports between columns at a certain time interval. Currently, the SMB process is applied to a separating and purifying process of p-xylene from aromatic hydrocarbon mixtures, a separation process of ethyl benzene, a separation process of chiral compounds and the like. One representative SMB process among SMB processes which are commercially practiced is disclosed in U.S. Pat. Nos. 4,326,092 and 5,382,747 applied by UOP LLC, normally referred as "Parex process".

Parex process is comprised of one or two long adsorption chambers connected in series, wherein the adsorbent chamber is divided into a number of adsorbent beds, normally 12 beds per adsorbent chamber. In a simulated moving bed adsorptive separation process like Parex process, the flow of a stationery phase is not practically realized. Instead, positions of inlet and outlet ports for desorbent, extract, fluid mixture(feed), raffinate and cleaning liquid are moved in the direction of the flow of a mobile phase at a certain time interval of rotary valve rotation, so as to move the columns in the counter direction relative to the flow direction of the mobile phase, with each port as the center, wherein the time interval of the rotary valve rotation is referred as switching time. As such, the virtual flow of the stationery phase can be made to simulate the counterflow to the flow of the mobile phase. The adsorbent used as a stationery phase is filled into the bed.

In Parex process, although each position of ports for desorbent, extract, fluid feed and raffinate cannot be continuously moved, similar effects can be obtained by providing a multiple access line and periodically switching each flow to adjacent line by using a rotary valve at a given time interval of switching time. During the process, a material with lower adsorption in the fluid feed mixture injected through a feed inlet port, comes out though a raffinate outlet port along the mobile phase, and a material with higher adsorption in the fluid feed mixture is adsorbed to each of adsorbent beds of the adsorbent chamber. As the column relatively moves at a certain switching time, the adsorbed material can be recovered through the extract outlet port after a certain time elapse.

However, the conventional Parex process for the production of p-xylene has a limit in improving productivity by using the SMB adsorptive separation process. In order to overcome the setback, a method called selective toluene disproportionation, STDP, has been developed for improving the concentration of p-xylene in the feed supplied to Parex process. In a process using a conventional crystallizer which is not SMB adsorptive separation process, a hybrid method comprising pretreatment in an adsorption tower for increasing the production has also been developed. However, these methods still have limitation in increasing the productivity to the desired extent.

SUMMARY OF THE INVENTION

With a view to solve the above-described problems of prior arts, the object of the present invention is to provide a simulated moving bed adsorptive separation process which can increase productivity, by subjecting the extracts eluted from a plurality of adsorption chambers arranged in parallel, to a crystallizer for additional separation, and a device used therein.

BRIEF DESCRIPTION OF MAIN SYMBOLS AND NUMERALS USED IN DRAWINGS

Figure 1:
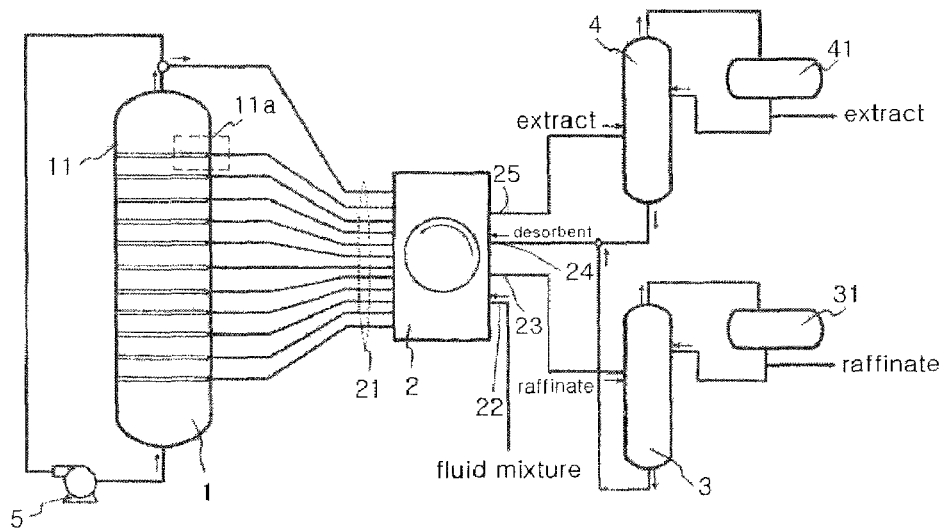
FIG. 1 is a schematic view illustrating a device used in a simulated moving bed (SMB) adsorptive separation process according to one embodiment of the present invention.

| | |
|---|---|
| 1: | adsorption chamber |
| 2: | rotary valve |
| 3: | raffinate column |
| 4: | final extraction column |
| 5: | circulation pump |
| 11: | bed |
| 12: | grid |
| 13: | bed line |
| 14: | center pipe |
| 21: | multiple access line |
| 22: | fluid mixture inlet port |
| 23: | raffinate outlet port |
| 24: | desorbent inlet port |
| 25: | extract outlet port |
| 31: | first separator |
| 41: | second separator |

DETAILED DESCRIPTION OF THE INVENTION

According to the present invention, provided is a simulated moving bed adsorptive separation process, using a device for the simulated moving bed adsorptive separation process which comprises: a plurality of adsorption chambers each chamber comprising a plurality of beds each bed containing a grid which is filled with adsorbent; a plurality of main rotary valves which connect each of the plurality of adsorption chambers, a fluid mixture inlet port, a raffinate outlet port, a desorbent inlet port and an extract outlet port to the multiple access line; an extract column for separating the extracts eluted from each of the plurality of the adsorption chamber through the extract outlet port, and turning back one of the separated fractions to the plurality of adsorption chambers and turning back the remnant fraction to a crystallizer as a feed for a crystallizer; a raffinate column for separating the raffinate from each of the plurality of the adsorption chambers through the raffinate outlet port, and turning back one of the separated fractions to the plurality of adsorption chambers; and a crystallizer which separate the desired component from the feed for a crystallizer, wherein the fluid mixture inlet port, the raffinate outlet port, the extract outlet port and the desorbent inlet port are moved to be connected to the adjacent multiple access line, by means of the rotation of the rotary valve at switching time, and comprising the steps of:
(a) contacting the fluid mixture with a solid adsorbent in the plurality of adsorption chambers and desorbing it with a desorbent so as to prepare each extract which comprises the desorbent and at least one component from the fluid mixture, and flowing each extract to a extract column.
(b) separating the each extract into a desorbent fraction which comprises mainly a desorbent and a fraction as a feed for a crystallizer which comprises mainly at least one component of the fluid mixture in the extract column, and turning back the desorbent fraction to the plurality of adsorption chambers; and
(c) separating a fraction which comprises mainly at least one component of the fluid mixture from the feed for a crystallizer in the crystallizer.

According to the simulated moving bed adsorptive separation process of the present invention, the feed for a crystallizer obtained from the extract column can be directly fed to the crystallizer or optionally can be transferred to a separate reservoir for future use.

Still further, according to the present invention, provided is a device for the simulated moving bed adsorptive separation process which comprises:

a plurality of adsorption chambers each chamber comprising a plurality of beds each bed containing a grid which is filled with adsorbent;

a plurality of main rotary valves which connect each of the plurality of adsorption chambers, a fluid mixture inlet port, a raffinate outlet port, a desorbent inlet port and an extract outlet port to the multiple access line;

an extract column for separating the extracts eluted from each of the plurality of the adsorption chamber through the extract outlet port, and turning back one of the separated fractions to the plurality of adsorption chambers and turning back the remnant fraction to a crystallizer as a feed for a crystallizer,;

a raffinate column for separating the raffinate from each of the plurality of the adsorption chambers through the raffinate outlet port, and turning back one of the separated fractions to the plurality of adsorption chambers; and a crystallizer which separate the desired component from the feed for a crystallizer, wherein the fluid mixture inlet port, the raffinate outlet port, the extract outlet port and the desorbent inlet port are moved to be connected to the adjacent multiple access line, by means of the rotation of the rotary valve at switching time.

According to the device for a simulated moving bed adsorptive separation process of the present invention, the extract column can be directly connected to the crystallizer in order to immediately transfer the feed for a crystallizer separated by the extract column to the crystallizer, or optionally the extract column can be connected to a separate reservoir for keeping the feed for a crystallizer in order to transfer it to the reservoir for future use.

Hereinafter, the present invention is further described in detail with the reference of the drawings attached to this specification.

Figure 4:
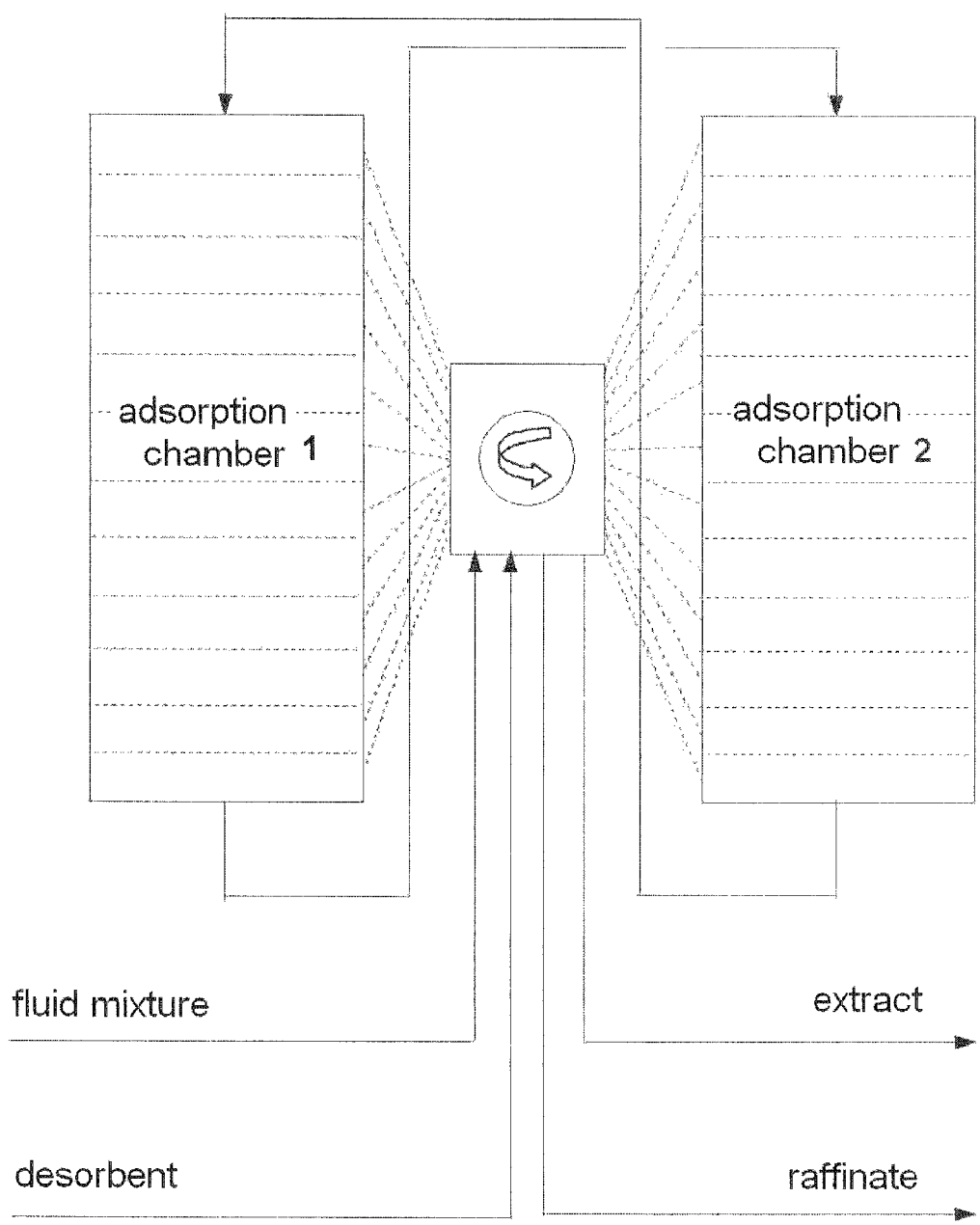
FIG. 4 is a schematic view of one embodiment of a conventional simulated moving adsorptive separation device which uses two adsorption chambers at the same time.

Each of FIGS. 1 and 4 is a schematic view illustrating one embodiment of a device used in conventional SMB separation process.

In the SMB adsorptive separation devices illustrated in FIGS. 1 and 4, two adsorption chambers having multiple layers of beds are provided, wherein each bed is filled with adsorbent. Each bed in the adsorption chambers is connected to a rotary valve through a multiple access line. The number of beds is traditionally 12 per chamber, however it is not specifically restricted to this.

The rotary valve connects each of two inlet ports and two outlet ports including a fluid mixture inlet port, a raffinate outlet port, a desorbent inlet port and an extract outlet port to the multiple access line. The detailed structure of the rotary valve is known to and easily practiced by a person who has ordinary knowledge in this art.

The raffinate column 3 recovers the raffinate from the raffinate outlet port 22 by using a first separator, and turns a portion of the raffinate back to the desorbent inlet port 24 as a desorbent.

The extract column 4 recovers the extract from the extract outlet port 25 by using a second separator, and turns a portion of the extract back to the desorbent inlet port 24 as a desorbent.

In SMB adsorptive separation process, the flow of a stationery phase is not practically realized. Instead, positions of ports for desorbent, extract, fluid mixture(feed) and raffinate are moved in the direction of the flow of a mobile phase at a certain time interval of switching, to move the columns in the counter direction relative to the flow direction of the mobile phase, with each port as the center. As such, the virtual flow of the stationery phase can be made to simulate the counterflow to the flow of the mobile phase. The adsorbent used as a stationery phase is filled into the bed.

Although each position of ports 22, 23, 24, 25 for desorbent, extract, fluid mixture(feed) and raffinate cannot be continuously moved, similar effects can be obtained by providing multiple access line 21 and periodically moving each flow to adjacent line by using a rotary valve 2 at a given time interval of switching time, as illustrated in FIGS. 1 and 4. During the process, a material with lower adsorption in the fluid feed mixture injected through a fluid feed inlet port comes out of a raffinate outlet port along the mobile phase, and a material with higher adsorption in the fluid feed mixture is adsorbed to each adsorbent bed 11 of the adsorbent chamber. As the column relatively moves at a certain switching time, the adsorbed material can be recovered through the extract outlet port 25.

Figure 5:
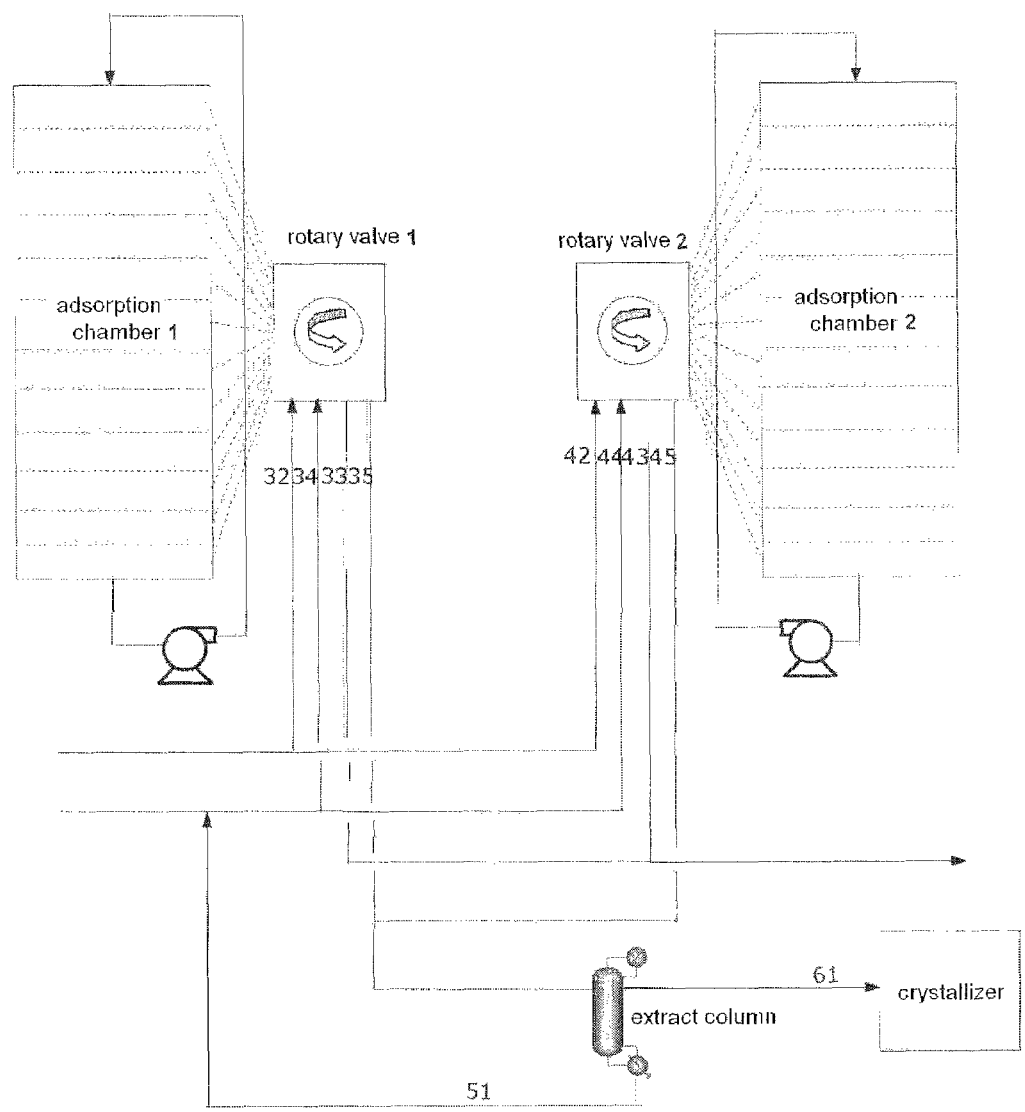
FIG. 5 is a schematic view of one embodiment of a simulated moving bed adsorptive separation device according to the present invention, which connects two adsorption chambers in parallel and subsequently using a crystallizer.

FIG. 5 is a schematic view of a device for a SMB adsorptive separation process according to one embodiment of the present invention. As seen from FIG. 5, the device for a SMB adsorptive separation process according to one embodiment of the present invention, unlike the device shown in FIGS. 1 and 4, employs a plurality of adsorption chambers, wherein the plurality of adsorption chambers are connected to each rotary valve through multiple access lines; separates each extract from each of the adsorption chambers into a desorbent and the feed for a crystallizer in the extract column; and then subjects the feed for a crystallizer to the crystallizer According to FIG. 5, in the device for a SMB adsorptive separation process according to the present invention, unlike the conventional Parex process, fluid mixtures 32, 42, i.e. feed, and desorbents 34, 44 are introduced into two adsorption chambers, then extracts 35, 45 and raffinates 33, 43 come out of two adsorption chambers. The extracts 35, 45 are fed to the extract column, in which the extracts are separated as a desorbent fraction 51 mainly comprising desorbent and a feed fraction for a crystallizer 61 which comprises mainly the components to be ultimately separated. The desorbent fraction 51 is turned back to said two adsorption chambers, and the feed fraction for a crystallizer 61 is transferred to the crystallizer. Meanwhile, other parts of the process such as further process for raffinates 33, 43 can be carried out as in the conventional Parex process.

Figure 2:
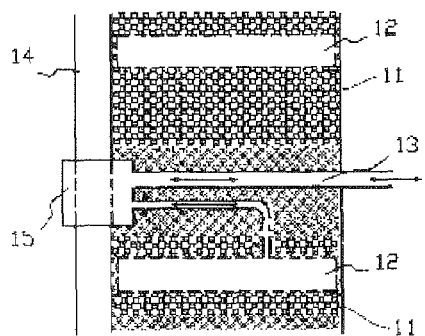
FIG. 2 is a magnified view of the part 11a of the device shown in FIG. 1, which is a schematic cross-sectional view of the bed in an adsorption chamber in a device according to one embodiment of the present invention.
Figure 3:
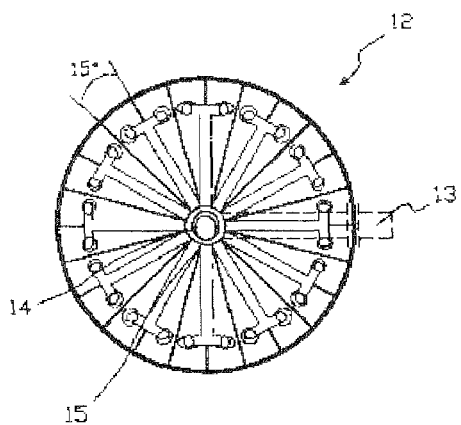
FIG. 3 is a plan view of a grid formed in the bed of an adsorption chamber in a device used for a simulated moving bed adsorptive separation process according to one embodiment of the present invention.

FIG. 2 is a magnified view of the part 11a illustrated in FIG. 1, which is a schematic cross-sectional view of a bed 11 in an adsorption chamber according to the present invention, and FIG. 3 is a plan view of a grid 12 formed in the bed 11 according to of the present invention.

As illustrated in FIG. 2, the bed 11 comprises a space for supporting the adsorbent therein, i.e. grid 12. The movement of the fluid flow between the upper and the lower beds is achieved through the grid 12. The grid 12 is connected to a center pipe distributor 15, and then to the multiple access line 21 through a bed line 13. As shown in FIG. 3, the grid 12 of the present invention is formed of two layers of screen, and thus served as a separating wall of the bed 11 by allowing only fluid flow to pass through. The grid 12 is comprised of pie-shaped 24 pieces.

As in the present invention, the extracts from a plurality of adsorption cambers are delivered to an extract column to be separated into a desorbent fraction and a feed fraction for a crystallizer, and then the feed fraction for a crystallizer from the extract column passes through the crystallizer. The purity of the feed fraction for a crystallizer is rather reduced as compared to the product obtained from the conventional Parex process, however the production rate is remarkably increased, resulting in significant improvement in productivity.

The present invention is further described in detail through the following example. However, the scope of the present invention is by no means restricted or limited by the example which has only illustrative purpose.

EXAMPLE AND COMPARATIVE EXAMPLE

In this example, a process for adsorptive separation of p-xylene from an aromatic hydrocarbon mixture which comprises other types of xylene isomers was carried out by using a SMB adsorptive separation device as shown in FIG. 5, in which extracts from a plurality of adsorption chambers were transferred to the extract column to separate them into a desorbent fraction and a feed fraction for a crystallizer, and the feed fraction for a crystallizer but from the extract column was subjected to the crystallizer for further separation. In the meantime, in a comparative example, the process was carried out by using the SMB adsorptive separation device as shown in FIG. 4, under the same process conditions as in the above example.

The final product was obtained as a result of the adsorptive separation of p-xylene, and the yield and purity of the final product, and production rate are summarized in Table 1 below.

TABLE 1

| | Use of crystallizer | Yield(%) | Purity (wt %) | Production rate (ton/hour) |
|---|---|---|---|---|
| Example | Used | 97 | 99.7 | 72 |
| Comparative example | Not used | 95 | 99.7 | 53 |

Note:
In the above table 1, the purity of the final product of the example (99.7 wt %) was the one obtained after the crystallizer, while the purity of the feed for a crystallizer, i.e. before passing the crystallizer, was 90.0 wt %.

As it is shown in Table 1, according to the example of the present invention, in which the extracts from a plurality of adsorption chambers are transferred to the extract column to obtain a desorbent fraction and a feed fraction for a crystallizer, and the feed fraction for a crystallizer from the extract column is subjected to a crystallizer for further separation, the production rate was increased by 35% or more as compared to the conventional process, accordingly the productivity on the whole was dramatically improved.

INDUSTRIAL AVAILABILITY

As it has been described so far, the present invention makes possible to significantly improve production rate in a SMB adsorptive separation process, thereby bringing a remarkable increase in productivity.

What is claimed is:

1. A simulated moving bed adsorptive separation process, using a device for the simulated moving bed adsorptive separation process which comprises: a plurality of adsorption chambers each chamber comprising a plurality of beds each bed containing a grid which is filled with adsorbent; a plurality of main rotary valves which connect each of the plurality of adsorption chambers, a fluid mixture inlet port, a raffinate outlet port, a desorbent inlet port and an extract outlet port to the multiple access line; an extract column for separating the extracts eluted from each of the plurality of the adsorption chambers through the extract outlet port, and turning back one of the separated fractions to the plurality of adsorption chambers and turning back the remnant fraction to a crystallizer as a feed for a crystallizer; a raffinate column for separating the raffinate from each of the plurality of the adsorption chambers through the raffinate outlet port, and turning back one of the separated fractions to the plurality of adsorption chambers; and a crystallizer which separate the desired component from the feed for a crystallizer, wherein the fluid mixture inlet port, the raffinate outlet port, the extract outlet port and the desorbent inlet port are moved to be connected to the adjacent multiple access line, by means of the rotation of the rotary valve at switching time, and comprising the steps of:

(a) contacting the fluid mixture with a solid adsorbent in the plurality of adsorption chambers and desorbing it with a desorbent so as to prepare each extract which comprises the desorbent and at least one component from the fluid mixture, and flowing each extract to a extract column;

(b) separating the each extract into a desorbent fraction which comprises mainly a desorbent and a fraction as a feed for a crystallizer which comprises mainly at least one component of the fluid mixture in the extract column, and turning back the desorbent fraction to the plurality of adsorption chambers; and (c) separating a fraction which comprises mainly at least one component of the fluid mixture from the feed for a crystallizer in the crystallizer.

2. The simulated moving bed adsorptive separation process according to claim 1, wherein the feed for a crystallizer obtained from the extract column is directly fed to the crystallizer.

3. The simulated moving bed adsorptive separation process according to claim 1, wherein the feed for a crystallizer obtained from the extract column is transferred to a separate reservoir.

4. A device for the simulated moving bed adsorptive separation process which comprises:
   a plurality of adsorption chambers each chamber comprising a plurality of beds each bed containing a grid which is filled with adsorbent;
   a plurality of main rotary valves which connect each of the plurality of adsorption chambers, a fluid mixture inlet port, a raffinate outlet port, a desorbent inlet port and an extract outlet port to the multiple access line;
   an extract column for separating the extracts eluted from each of the plurality of the adsorption chambers through the extract outlet port, and turning back one of the separated fractions to the plurality of adsorption chambers and turning back the remnant fraction to a crystallizer as a feed for a crystallizer;
   a raffinate column for separating the raffinate from each of the plurality of the adsorption chambers through the raffinate outlet port, and turning back one of the separated fractions to the plurality of adsorption chambers; and
   a crystallizer which separate the desired component from the feed for a crystallizer,
   wherein the fluid mixture inlet port, the raffinate outlet port, the extract outlet port and the desorbent inlet port are moved to be connected to the adjacent multiple access line, by means of the rotation of the rotary valve at switching time.

5. The device for the simulated moving bed adsorptive separation process according to claim 4, wherein the extract column is directly connected to the crystallizer.

6. The device for the simulated moving bed adsorptive separation process according to claim 4, wherein the extract column is connected to a reservoir for keeping the feed for a crystallizer.

* * * * *